(12) United States Patent
Shepard (10) Patent No.: US 8,926,326 B2
(45) Date of Patent: Jan. 6, 2015

(54) DENTURE RETENTION SYSTEM

(76) Inventor: John S. Shepard, Fort Collins, CO (US)

( * ) Notice: Subject to any disclaimer, the term of this patent is extended or adjusted under 35 U.S.C. 154(b) by 0 days.

(21) Appl. No.: 13/565,934

(22) Filed: Aug. 3, 2012

(65) Prior Publication Data

US 2014/0038133 A1 Feb. 6, 2014

(51) Int. Cl.
*A61C 8/00* (2006.01)

(52) U.S. Cl.
USPC .......................................... 433/173; 433/177

(58) Field of Classification Search
USPC .................... 433/167, 171–178, 201.1, 168.1
See application file for complete search history.

(56) References Cited

U.S. PATENT DOCUMENTS

| | | | |
|---|---|---|---|
| 2,112,007 A | 3/1938 | Adams | |
| 3,921,293 A * | 11/1975 | Keumurdji | 433/168.1 |
| 4,204,321 A * | 5/1980 | Scott | 433/177 |
| 4,431,416 A * | 2/1984 | Niznick | 433/174 |
| 4,787,851 A | 11/1988 | Kusano | |
| 5,030,094 A * | 7/1991 | Nardi et al. | 433/169 |
| 5,049,072 A | 9/1991 | Lueschen | |
| 5,092,770 A * | 3/1992 | Zakula | 433/172 |
| 5,098,295 A * | 3/1992 | Durr et al. | 433/172 |
| 5,417,570 A | 5/1995 | Zuest et al. | |
| 5,520,540 A | 5/1996 | Nardi et al. | |
| 5,556,280 A * | 9/1996 | Pelak | 433/172 |
| 5,662,475 A * | 9/1997 | Mena | 433/172 |
| 5,678,997 A | 10/1997 | De Buck | |
| 5,885,077 A | 3/1999 | Jeffer | |
| 5,997,300 A | 12/1999 | Tseng | |
| 6,302,693 B1 * | 10/2001 | Mena | 433/172 |
| 6,506,052 B1 | 1/2003 | Hoffman | |
| 6,685,473 B2 | 2/2004 | Weissman | |
| 6,981,871 B2 | 1/2006 | Mullaly et al. | |
| 7,234,940 B2 | 6/2007 | Weissman | |
| 7,431,589 B2 | 10/2008 | Weissman | |
| 7,758,346 B1 | 7/2010 | Letcher | |
| 7,785,108 B2 | 8/2010 | Tache et al. | |
| 7,959,439 B2 * | 6/2011 | Bulloch et al. | 433/173 |
| 7,985,071 B2 | 7/2011 | Weissman | |
| 2005/0019730 A1 * | 1/2005 | Gittleman | 433/174 |
| 2006/0269903 A1 * | 11/2006 | Bulard et al. | 433/174 |
| 2009/0263761 A1 * | 10/2009 | Shepard | 433/174 |
| 2009/0263762 A1 * | 10/2009 | Shepard | 433/174 |
| 2009/0263763 A1 * | 10/2009 | Shepard | 433/174 |

* cited by examiner

*Primary Examiner* — Cris L Rodriguez
*Assistant Examiner* — Hao D Mai
(74) *Attorney, Agent, or Firm* — Ancel W. Lewis, Jr.

(57) ABSTRACT

A denture retention system includes a denture, abutments and an implant connected to each abutment. The denture has an inner channel with a resilient liner and engaging caps in the inner channel that releasably retain the denture on the abutments. The engaging caps each have a cavity that receives the head of an abutment. The cavities are sized with longitudinal space for the heads of the abutments so that the denture rests on the gingival tissue while the abutments restricts movement of the denture away from the gingival tissue. The system can be used with large diameter or mini implants. The separate implant and abutment allow precise selection of the abutment height. The abutment has a spherical head with tool engageable flats for tightening the abutment onto the implant.

16 Claims, 7 Drawing Sheets

DENTURE RETENTION SYSTEM

TECHNICAL FIELD

The present invention relates to dentistry and more particularly to a system for releasably locating, supporting and retaining a denture.

BACKGROUND ART

Dental implants are used to support one or more artificial teeth. Implants can help support, stabilize and retain full dentures. Suction aids retention of upper full dentures, but suction is generally inadequate for retention of lower full dentures.

At present there are two kinds of dentures, generally termed "hard dentures" and "soft dentures". Hard dentures are made out of any type of plastic and are unlined. Soft dentures have a rigid structure with a liner made of a soft, cushioning material, such as silicone, in the inner channel over the patient's gingival tissue. Some prior known implants systems for dentures use a ball shaped abutment that projects from each implant. Hard dentures are retained by screws that extend through the denture and into the implants. An alternative system for retaining hard dentures has a cap or holder imbedded in the channel of the denture. The cap has a rubber or elastomeric "O" ring that snaps over a ball shaped abutment on the implant. The implants support the hard dentures with these retention systems and the forces of chewing are on the implants.

The liner in a soft denture is intended to cushion and support the denture on the gingival tissues. One known system for retaining a soft denture has cavities opening into the inner channel. The liner extends into and lines the cavities, and shaped abutments on the implants protrude into the cavities to retain the denture. These systems require complex cavity and abutment shapes in order to provide sufficient retention.

There are two main types of implant systems currently in use. The first type uses what is generally known as a large diameter implant and is greater than 3 mm in diameter. This system is generally a two piece system that includes an implant with an internally threaded cavity and an abutment that threads into the cavity in the implant. The large diameter implant system is very stable after it fuses to the bone, allows precise selection of the abutment height after the implant is installed, and after years of use the abutment neck height can be changed to accommodate receding tissues. However, the large diameter implant is more difficult to place by the General Dentist and is most often placed by a specialist, is more expensive to make and install, has a higher risk of damage to the nerves in the bone, and there is usually a 2 to 3 month wait for the bone to fuse to the implant.

The second type of implant system uses what is generally known as a mini or small diameter implant with the implant diameter being less than about 3 mm. Since the diameter of the implant is substantially too small for a cavity with internal threads, in this system the implant and abutment are generally one piece. The mini implant is easy for the General Dentist to install, is less expensive to make and install, is usually easier to place, has a lower risk of damage to the nerves in the bone, is screwed tightly into the bone without invasive surgery and can be loaded immediately. However, the mini implant is smaller and thus less stable under heavy loads, and can be placed by less trained dentists, resulting in the risk of abuse and misplacement. The one piece mini implant is harder to get the correct length, and can protrude too far into the denture base, such that a soft denture is supported by the implant instead of the gingival tissue.

U.S. Pat. No. 4,787,851 to Kusano, et al. discloses a denture having an inner channel with an elastomeric liner and ball shaped abutments that project into the liner. U.S. Pat. No. 2,112,007 to Adams discloses a denture having an inner channel with snap ring cup sockets and ball shaped abutments that project into the sockets. U.S. Pat. No. 5,049,072 to Lueschen discloses a denture having an inner channel with sockets, o-rings and ball shaped abutments that project into the sockets.

There is a need for a denture retention system that sufficiently retains the denture while allowing the gingival tissue to support the denture. In such a system there is the further need of being able to precisely select the abutment height and to adjust the abutment height to accommodate receding tissues, with both large diameter and mini implants.

DISCLOSURE OF THE INVENTION

A system for retaining a denture on gingival tissue, where the denture has an outer side with a plurality of artificial teeth, an inner side with an inner channel, and a resilient liner in the inner channel, includes at least one abutment, a substantially rigid engaging cap for each abutment, and an implant for each abutment. The abutment has a substantially spherical head, a neck connected to the head and a base connected to the neck. The neck has a diameter smaller than said head. The engaging cap is rigidly mounted in the denture. The engaging cap has an end portion with a first face and a spaced second face, and an enclosing fence formed by a plurality of spaced fingers that project transversely from the second face to define a cavity with an open end. The cavity is sized to receive the head of the abutment. The fingers each have an inwardly projecting lip portion opposite the end portion to retain the head in the cavity. The cavity is sized longitudinally to space the head from the end portion when the lip portions contact the head so that the liner supports the denture on the gingival tissue while the abutment restricts movement of the denture away from the gingival tissue. The head of the abutments has a plurality of spaced, tool engageable flats for tightening the abutment on the implant. Large diameter and mini implants can be used with the system.

BRIEF DESCRIPTION OF THE DRAWINGS

Details of this invention are described in connection with the accompanying drawings that bear similar reference numerals in which.

DETAILED DESCRIPTION OF THE INVENTION

Figure 1:
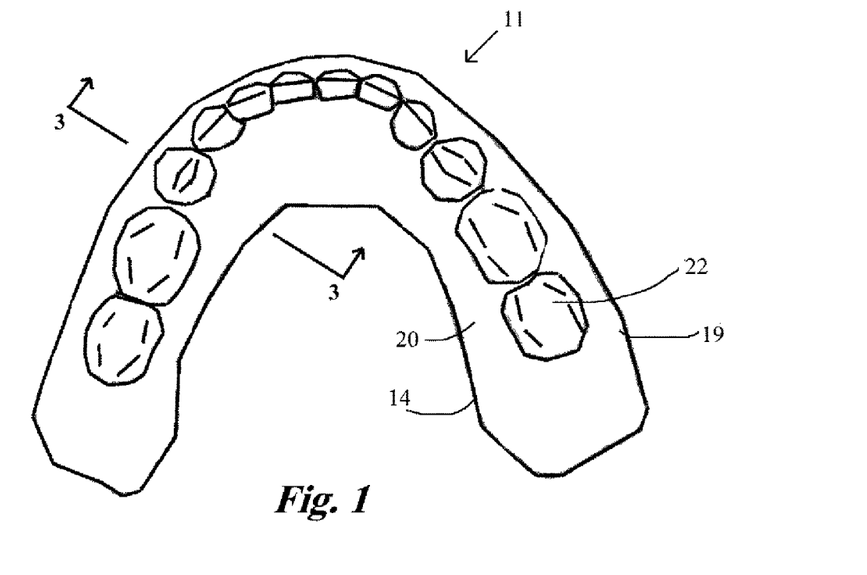
FIG. 1 is a top plan view of a denture retaining system embodying features of the present invention.
Figure 2:
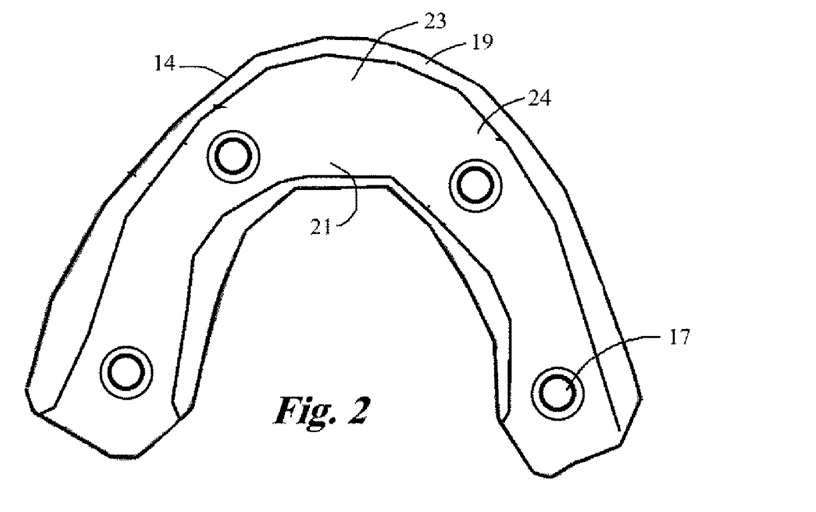
FIG. 2 is a bottom plan view of a denture of the system of FIG. 1.
Figure 3:
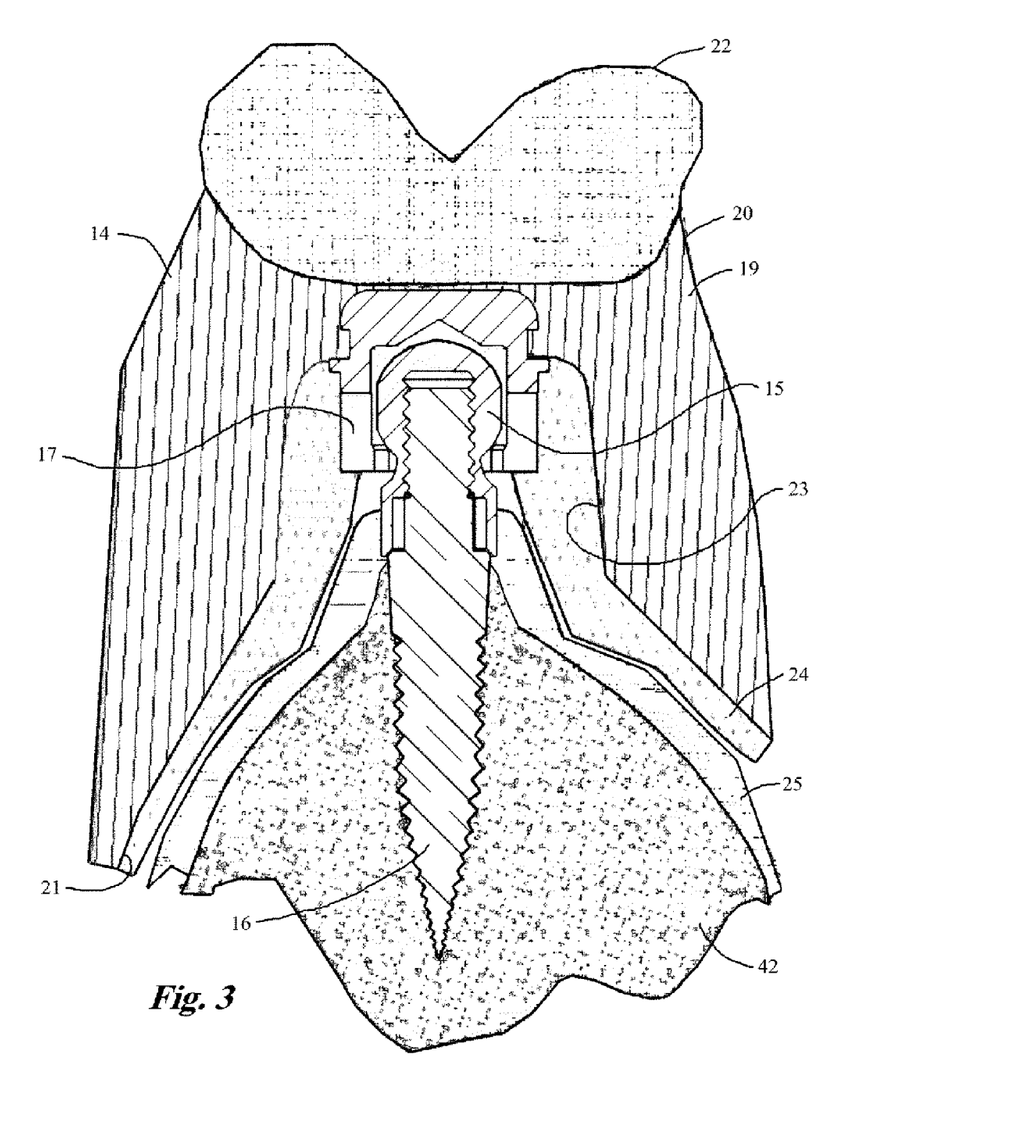
FIG. 3 is a sectional view of the system of FIG. 1 taken along line 3-3.

Referring to FIGS. 1 to 3, a system 11 for releasably retaining a denture 14 includes abutments 15, implants 16 and engaging caps 17. Generally, four abutments 15 are used, with an implant 16 and an engaging cap 17 for each abutment 15. The denture 14 has a body 19 with an outer side 20 and a spaced inner side 21. The outer side 20 is shaped to simulate the appearance of gums and a plurality of artificial teeth 22 are mounted on the outer side 20. The inner side 21 has an inner channel 23 that is shaped to receive the gums or gingival tissue 25 of a patient. The inner channel 23 includes a resilient liner 24. The liner 24 is made of a soft, cushioning material such as an elastomer. The liner 24 is preferably made of a medical silicone. By way of example, and not as a limitation, the liner 24 can be made of Medical Silicone Adhesive 0247 by Dow-Corning.

Figure 4:
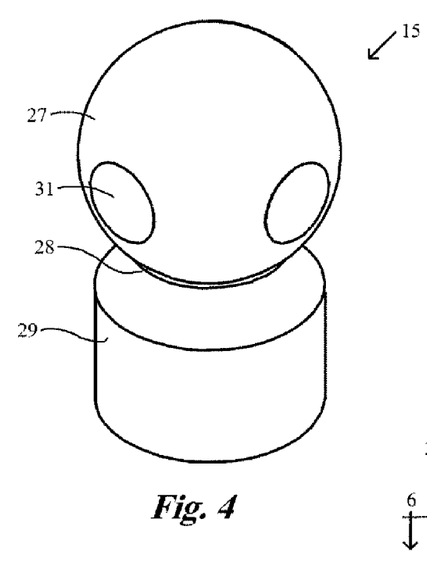
FIG. 4 is a perspective view of an abutment of the system of FIG. 1.
Figure 5:
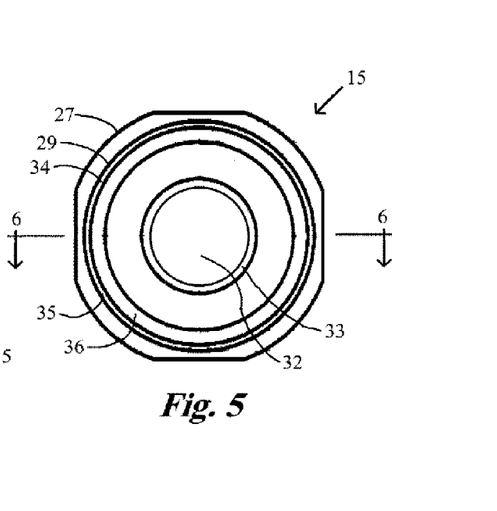
FIG. 5 is a bottom plan view of the abutment of FIG. 4.
Figure 6:
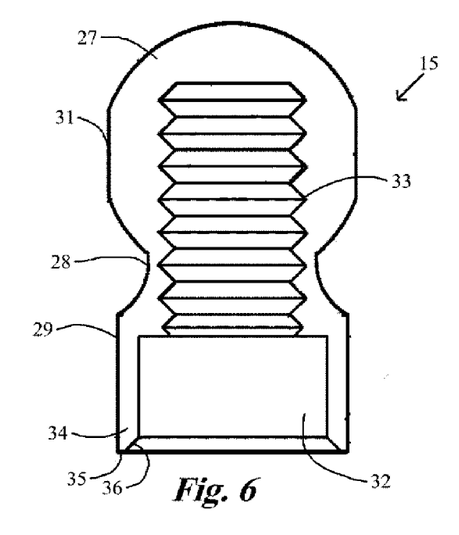
FIG. 6 is a sectional view of the abutment of FIG. 4 taken along line 6-6 of FIG. 5.

As shown in FIGS. 4-6, the abutment 15 has a head 27, a neck 28 connected to the head 27 and a base 29 connected to the neck 28 opposite the head 27. The head 27 is substantially spherical. The neck 28 curves inwardly from the head 27 and then outwardly to the base 29, and has a diameter that is less than the diameter of the head 27 and less than the diameter of the base 29. The base 29 is substantially cylindrical.

The head 27 has a plurality of spaced, radially outwardly facing flats 31. The flats 31 can be engaged by a tool, such as a socket, to tighten the abutment 15. The head 27 shown has four flats 31. Preferably the flats 31 are uniformly spaced and the head 27 has at least four flats 31.

A cylindrical abutment aperture 32 with internal threads 33 extends into the abutment 15 from the base 29, opposite the neck 28. A hollow, cylindrical skirt 34 projects from the periphery of the base 29, opposite the neck 28. The end 35 of the skirt 34, opposite the base 29, has an inwardly facing bevel or taper 36.

Figure 7:
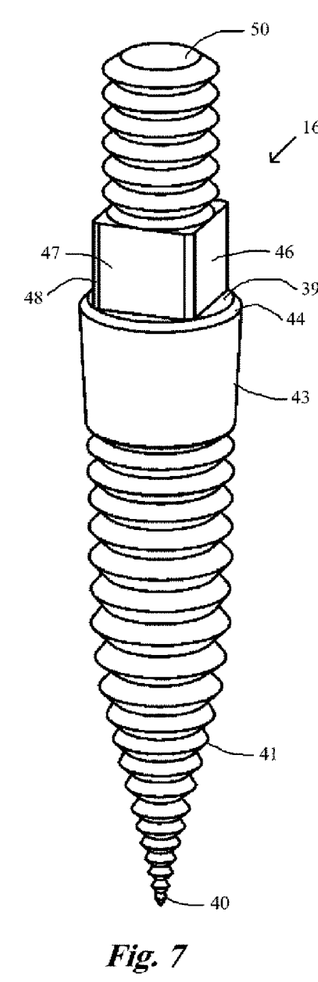
FIG. 7 is a perspective view of an implant for the abutment of FIG. 4.

Referring to FIG. 7, the implant 16 has a first end 39, a spaced second end 40, external threads 41 extending from the second end 40 towards the first end 39 for threading the implant 16 into alveolar bone 42, and a cylindrical surface 43 between the threads 41 and the first end 39. A outward bevel or taper 44 connects the cylindrical surface 43 and the first end 39. The taper 44 at the first end 39 of the implant 16 is complementary to the taper 36 on the skirt 34 of the abutment 15.

A tool engageable section 46 projects from the first end 39 of the implant 16. The tool engageable section 46 has a plurality of spaced, radially outwardly facing flats 47 that are connected by corners 48. The corners 48 can be flat or rounded. Preferably the flats 47 are uniformly spaced around the tool engageable section 46. The tool engageable section 46 shown has four flats 47. Other numbers of flats 47 can be used.

An externally threaded abutment connecting member 50 projects from the tool engageable section 46, opposite the first end 39 of the implant 16. The abutment connecting member 50 is sized to thread into the abutment aperture 32. When the abutment 15 is threaded onto the implant 16, the corners 48 on the tool engageable section 46 allow the skirt 34 to fit over the tool engageable section 46, and the taper 36 on the skirt 34 seats on the taper 44 at the first end 39 of the implant 16, to provide a tight fit and to secure the abutment 15 on the implant 16. The height of each abutment 15 can then be precisely selected with the two piece system of abutment 15 and implant 16. The structure of the implant 16 with the abutment 15 can be used as a two piece mini implant system, as well as a large diameter implant system.

Figure 8:
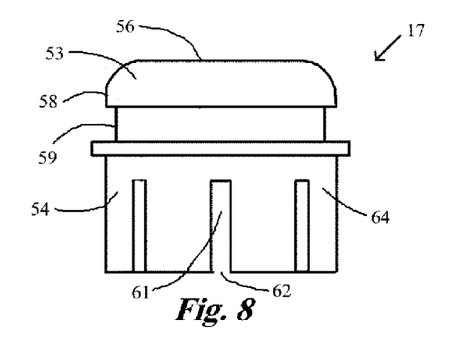
FIG. 8 is a side elevation view of an engaging cap for the system of FIG. 1.
Figure 9:
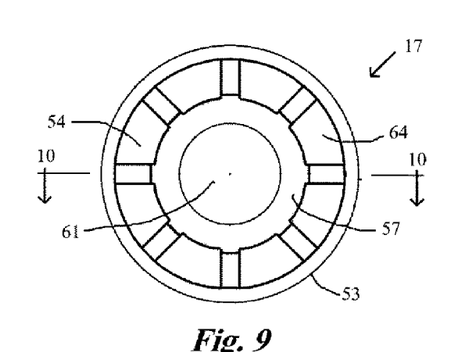
FIG. 9 is a bottom plan view of the engaging cap of FIG. 8.
Figure 10:
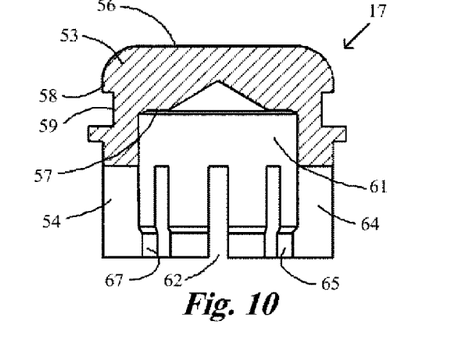
FIG. 10 is a sectional view of the engaging cap of FIG. 8 taken along line 10-10 of FIG. 9.

FIGS. 8-10 show the engaging cap 17, including an end portion 53 and a fence 54. The engaging cap 17 is made of a rigid, elastic material. Preferably the engaging cap 17 is made of metal, and more preferably the engaging cap 17 is made of titanium or a titanium alloy. The end portion 53 has a substantially circular cross-section with a rounded first face 56, a spaced, substantially flat second face 57 and a peripheral surface 58 connecting the first and second faces 56 and 57. The peripheral surface 58 has an outwardly facing, annular channel 59. The annular channel 59 is filled with the rigid plastic of the denture 14 when the denture 14 is molded to secure the engaging cap 17 in the denture.

The fence 54 projects transversely from the second face 57 to define a hollow, cylindrical cavity 61 with an open end 62 opposite the end portion 53. The fence 54 shown includes a plurality of spaced fingers 64 that project transversely from the second face 57 of the end portion 53. The fingers 64 each have a radially inwardly projecting lip portion 65 opposite the end portion 53. As shown in FIG. 3, the cavity 61 is sized to receive head 27 of the abutment 15. The lip portions 65 on the fingers 64 retain the head 27 in the cavity 61. The fingers 64 flex outwardly when the engaging cap 17 is pushed onto the head 27 of the abutment 15 to engage the abutment 15 with the engaging cap 17 and when the engaging cap 17 is pulled away from the abutment 15 to release the head 27 of the abutment 15 from the cavity 61. The fingers 64 with the lip portions 65 provide a means 67 for releasably retaining the head 27 in the cavity 61. Other means for releasably retaining the head 27 in the cavity 61 can be used.

The cavity 61 is sized longitudinally so that the head 27 is spaced from the end portion 53 when the means 67 for releasably retaining the head 27 in the cavity 61 contacts the head 27. The height of each abutment 15 can then be precisely selected so that the denture 14 is supported on the gingival tissue 25 by the liner 24, instead of being supported by the abutments 15 and implants 16, while the abutments 15 restrict movement of the denture 14 away from the gingival tissue 25. Chewing forces are thereby exerted against the liner instead of through the abutments 15 to the implants 16. The size of the head 27 of the abutment 15 relative to the cavity 61 can be selected to modify the retention force of the denture 14 by the engaging caps 17. A larger head 27 will provide a greater retention force while a smaller head 27 will provide a lower retention force.

The inner channel 23 is shaped to receive the gingival tissue 25. The inner channel 25 has a base and opposed sides extending away from the base and terminate in two ends. The resilient liner 24 extends into inner channel 24 along the sides from the two ends to contact the engaging cap 17 and surrounds each engaging cap across the base of the inner channel.

Figure 11:
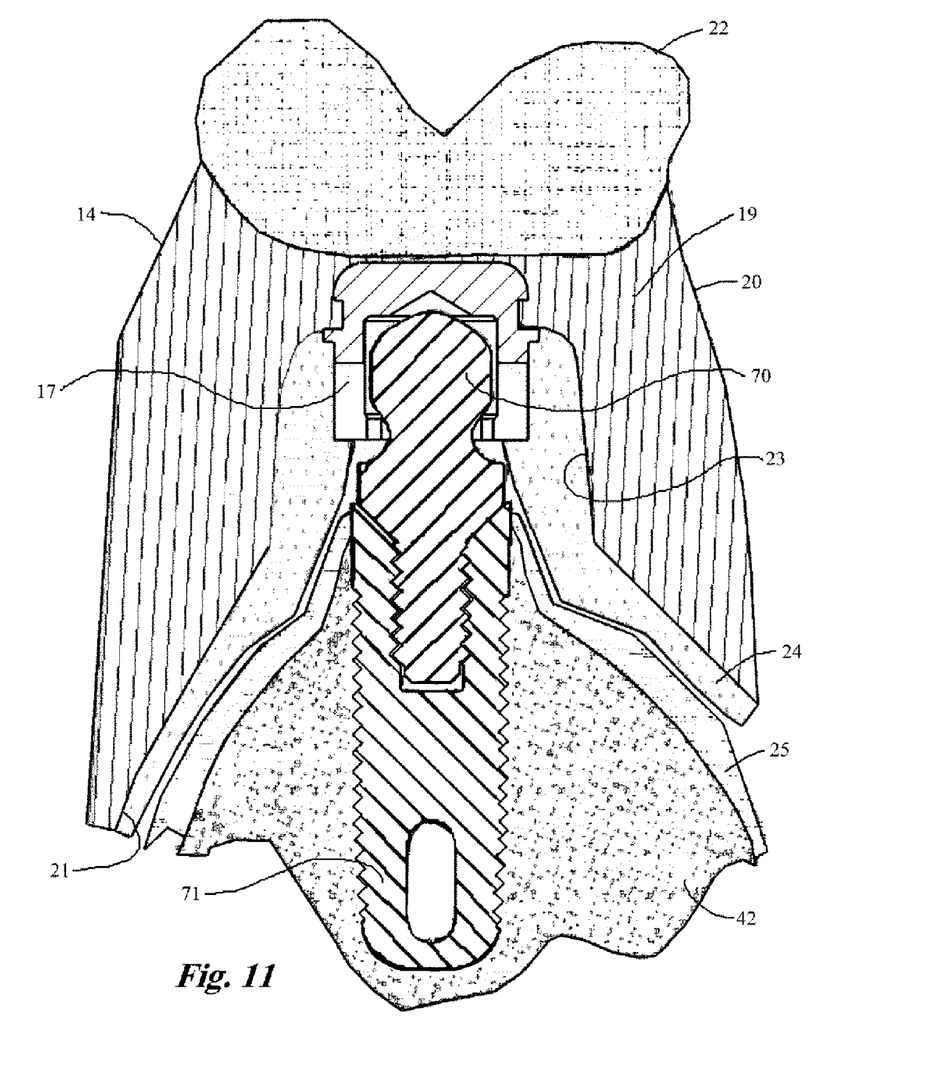
FIG. 11 is a sectional view of the system of FIG. 1 taken along line 3-3 of FIG. 2, with an another abutment and implant.

FIG. 11 shows the system 11 for releasably retaining a denture 14 with another abutment 70 and another implant 71.

Figure 12:
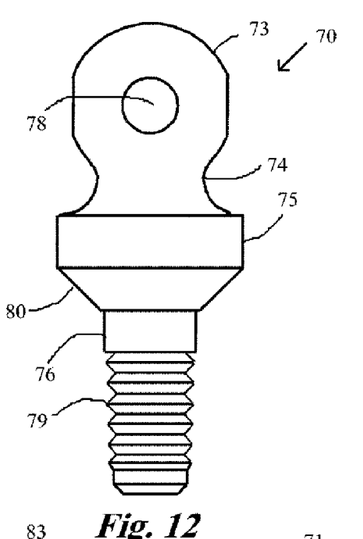
FIG. 12 is a side elevation view of the abutment of FIG. 11.

As shown in FIG. 12, the abutment 70 has a head 73, a neck 74 connected to the head 73, a base 75 connected to the neck 74 opposite the head 73, and an implant connecting member 76 that projects from the base 75 opposite the neck. The neck 74 curves inwardly from the head 73 and then outwardly to the base 75, and has a diameter that is less than the diameter of the head 73 and less than the diameter of the base 75. The base 75 is substantially cylindrical.

The head 73 has a plurality of spaced, radially outwardly facing flats 78. The flats 78 can be engaged by a tool, such as a socket, to tighten the abutment 70. The head 73 shown has four flats 78. Preferably the flats 78 are uniformly spaced and the head 73 has at least four flats 78. The implant connecting member 76 has external threads 79 that are spaced from the base 75 and an inward taper 80 from the base 75 to the threads 79.

Figure 13:
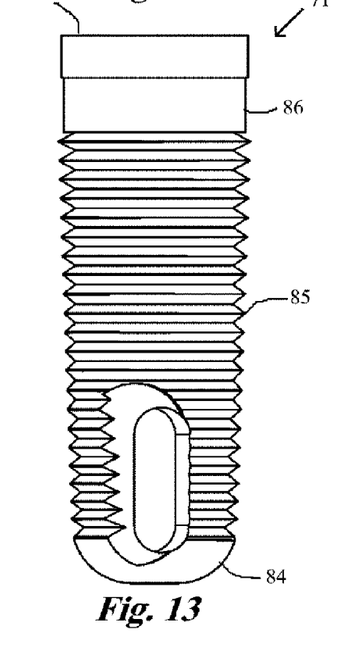
FIG. 13 is a side elevation view of the implant of FIG. 11.
Figure 14:
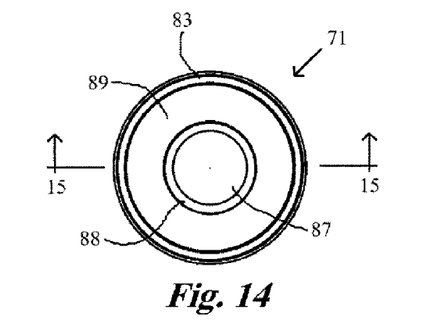
FIG. 14 is a top plan view of the implant of FIG. 13.
Figure 15:
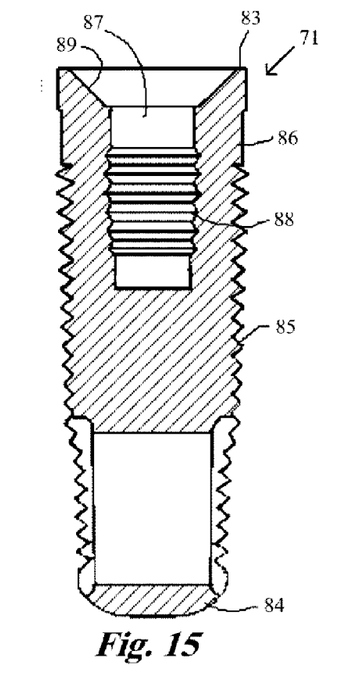
FIG. 15 is a sectional view of the implant of FIG. 13 taken along line 15-15 of FIG. 14.

Referring to FIGS. 13-15, the implant 71 has a first end 83, a spaced second end 84, external threads 85 extending from the second end 84 towards the first end 83 for threading the implant 71 into alveolar bone 42, and a cylindrical surface 86 between the threads 85 and the first end 83. An abutment aperture 87 extends into the implant 71 from the first end 83. The abutment aperture 87 has internal threads 88 that are spaced from the first end 83 and an inward taper 89 between the first end 83 and threads 88.

The abutment aperture 87 is sized to receive the implant connecting member 76 on the abutment 70, and the taper 89 of the abutment aperture 87 is complementary to the taper 80 of the implant connecting member 76. When the abutment 70 is threaded onto the implant 71, the taper 80 of the implant connecting member 76 seats on the taper 89 of the abutment aperture 87, to provide a tight fit and to secure the abutment 70 on the implant 71. The height of each abutment 70 can then be precisely selected with the two piece system of abutment 70 and implant 71.

Figure 16:
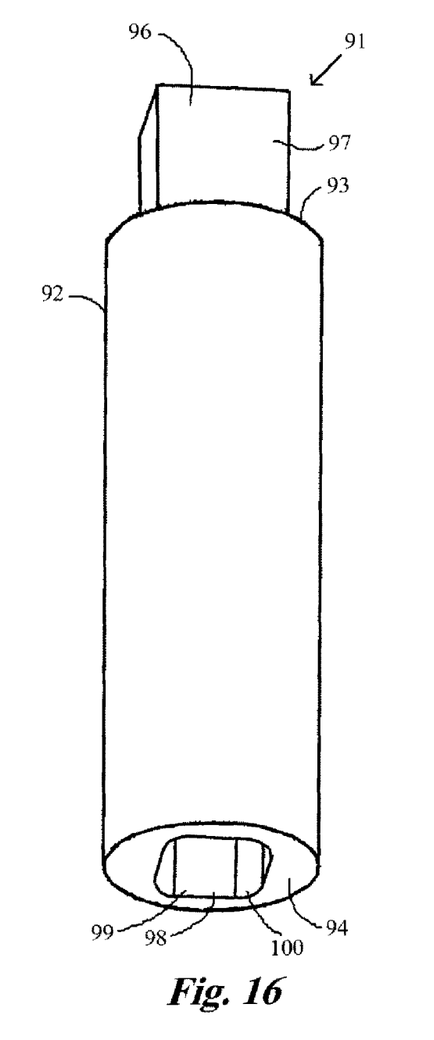
FIG. 16 is a perspective view of a tool for tightening the abutments of FIGS. 3 and 11.

FIG. 16 shows a tool 91 for tightening the abutment 15 or the abutment 70, including a cylindrical body 92 with a first end 93 and a spaced second end 94, a tool engageable portion 96 at the first end 93 having a plurality of flats 97, and an interior cavity 98 that extends into the body 92 from the second end 94. The interior cavity 98 has a substantially uniform cross-section with a plurality of spaced flats 99 connected by corners 100. The interior cavity 98 is sized to fit over the head 27 of abutment 15 or the head 73 of abutment 70 with the flats 99 of the interior cavity 98 engaging the flats 31 on the head 27 or the flats 78 on the head 73.

Figure 17:
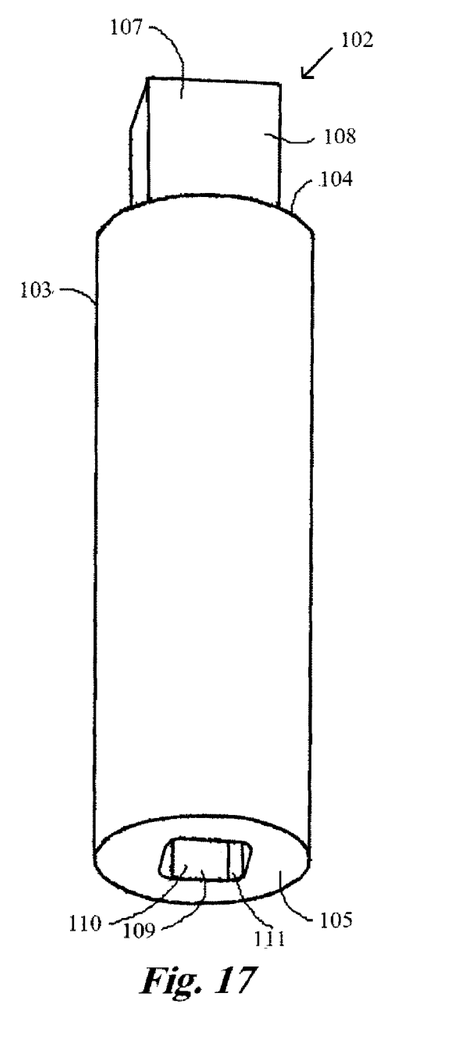
FIG. 17 is a perspective view of a tool for tightening the implant of FIG. 7.

As shown in FIG. 17 a tool 102 for tightening the implant 16 includes a cylindrical body 103 with a first end 104 and a spaced second end 105, a tool engageable portion 107 at the first end 104 with a plurality of flats 108, and an interior cavity 109 that extends into the body 103 from the second end 105. The interior cavity 109 has a substantially uniform cross-section with a plurality of spaced flats 110 connected by corners 111. The interior cavity 109 is sized to fit over the abutment connecting member 50 and the tool engageable section 46 of the implant 16 with the flats 110 of the interior cavity 109 engaging the flats 47 on the tool engageable section 46.

Although the present invention has been described with a certain degree of particularity, it is understood that the present disclosure has been made by way of example and that changes in details of structure may be made without departing from the spirit thereof.

What is claimed is:

1. A system for retaining a denture on gingival tissue, said denture having an outer side with a plurality of artificial teeth and an inner side having an inner channel shaped to receive said gingival tissue, said inner channel having a base and opposed sides extending away from said base and terminating in two ends, comprising:

at least one abutment, said abutment having a substantially spherical head, a neck connected to said head and a base connected to said neck, said neck having a diameter smaller than said head, an implant for each said abutment, said implant having a first end, a spaced second end, and external threads extending from said second end towards said first end for threading said implant into alveolar bone, said first end of said implant releasably, threadedly connecting to said base of said abutment, an engaging cap for each said abutment rigidly mounted in said denture, said engaging cap having an end portion with a first face and a spaced second face opposite said first face, and an enclosing fence that projects transversely from said second face to define a cavity with an open end opposite said end portion, said cavity being sized to receive said head, said engaging cap including means, connected to said fence at said open end, for releasably retaining said head in said cavity, said cavity being sized longitudinally to define a space between said head and said end portion when said means for releasably retaining said head contacts said head, and a resilient liner in said inner channel, said liner extending into said inner channel along said sides from said two ends to contact said engaging cap, said liner surrounding said engaging cap across said base of said inner channel, said liner supporting said denture on said gingival tissue, said liner compensating for the sponginess and surface irregularities in the gingival tissue so that the chewing forces are more uniformly distributed over the whole surface area of gingival tissue and said space is maintained during chewing wherein said abutment has a height that is selected such that said liner supports said denture on said gingival tissue so that chewing forces on said denture are transmitted from said denture through said liner to said gingival tissue and said space remains during chewing so that no chewing forces are transmitted from said denture to said abutment while said abutment restricts movement of said denture away from said gingival tissue.

2. The system as set forth in claim 1 wherein said fence includes a plurality of fingers that project transversely from said second face and said means for releasably retaining said head includes radially inwardly projecting lip portions on said fingers at said open end, whereby said fingers flex outwardly when said engaging cap is pushed onto said head and when said engaging cap is pulled off of said head.

3. The system as set forth in claim 1 wherein said head of said abutment has a plurality of radially outwardly facing, tool engageable flats for tightening said abutment on said implant.

4. The system as set forth in claim 3 wherein said abutment has at least four said flats.

5. The system as set forth in claim 3 including a tightening tool, said tool having an interior cavity with a substantially uniform cross section sized and shaped to fit over and engage said flats on said head of said abutment to tighten said abutment on said implant.

6. The system as set forth in claim 1 wherein said implant has an externally threaded abutment connecting member that projects from said first end, and said abutment has an abutment aperture extending inwardly from said base, said abutment aperture having internal threads and being sized and shaped to receive said abutment connecting member.

7. The system as set forth in claim 1 wherein said implant has a tool engageable section that projects from said first end and an externally threaded abutment connecting member that projects from said tool engageable section, said abutment has an abutment aperture extending inwardly from said base, said abutment aperture having internal threads and being sized and shaped to receive said abutment connecting member, said tool engageable section having a plurality of radially outwardly facing, tool engageable flats for tightening said implant in said alveolar bone.

8. The system as set forth in claim 7 wherein said tool engageable section has rounded corners between said flats and said abutment includes a hollow, cylindrical skirt that projects from said base opposite said neck, said skirt being sized to fit over said rounded corners on said tool engageable section of said implant and contact said implant at said first end.

9. The system as set forth in claim 8 wherein said first end of said implant has an inward taper and said skirt has a complementary taper opposite said base,
whereby, when said abutment is tightened, said taper on said skirt seats on said taper on said first end of said implant to secure said abutment on said implant.

10. The system as set forth in claim 1 wherein said abutment has an implant connecting member, with external threads, that projects from said base opposite said neck, and said implant has a abutment aperture that extends into said implant from said first end, said abutment aperture having internal threads and being sized to threadedly receive said implant connecting member.

11. The system as set forth in claim 10 wherein said implant connecting member has an inward taper from said base to said external threads and said abutment aperture has a complementary taper from said first end to said internal threads,
whereby when said abutment is tightened, said taper on said implant connecting member seats on said taper in said abutment aperture to secure said abutment on said implant.

12. The system as set forth in claim 1 wherein said engaging cap is made of metal.

13. The system as set forth in claim 1 wherein said engaging cap is made of titanium.

14. The system as set forth in claim 1 wherein said end portion of said engaging cap has a radially outwardly facing, annular channel for securing said engaging cap in said denture.

15. A system for retaining a denture on gingival tissue, said denture having an outer side with a plurality of artificial teeth, and an inner side having an inner channel shaped to receive said gingival tissue, said inner channel having a base and opposed sides extending away from said base and terminating in two ends, comprising:
at least one abutment, said abutment having a substantially spherical head, a neck connected to said head and a base connected to said neck, said neck having a diameter smaller than said head, said head of said abutment having a plurality of radially outwardly facing, tool engageable flats,
an engaging cap for each said abutment rigidly mounted in said denture, said engaging cap having an end portion with a first face and a spaced second face opposite said first face, and a plurality of fingers that project transversely from said second face to define a cavity with an open end opposite said end portion, said cavity being sized to receive said head, said fingers each having a radially inwardly projecting lip portion at said open end for releasably retaining said head in said cavity, said cavity being sized longitudinally to define a space between said head and said end portion when said lip portions contact said head, an implant for each said abutment having a first end, a spaced second end, and external threads extending from said second end towards said first end for threading said implant into alveolar bone, said first end of said implant releasably, threadedly connecting to said base of said abutment, and
a resilient liner in said inner channel, said liner extending into said inner channel along said sides from said two ends to contact said engaging cap, said liner surrounding said engaging cap across said base of said inner channel, said liner supporting said denture on said gingival tissue, said liner compensating for the sponginess and surface irregularities in the gingival tissue so that the chewing forces are more uniformly distributed over the whole surface area of gingival tissue and said space is maintained during chewing
wherein said abutment has a height that is selected such that said liner supports said denture on said gingival tissue so that chewing forces on said denture are transmitted from said denture to said gingival tissue and said space remains during chewing so that no chewing forces are transmitted from said denture to said abutment while said abutment restricts movement of said denture away from said gingival tissue,
whereby said abutment is tightened on said implant with said tool engaging flats.

16. A system for retaining and supporting a denture on gingival tissue, said denture having an outer side with a plurality of artificial teeth, and an inner side having an inner channel shaped to receive said gingival tissue, said inner channel having a base and opposed sides extending away from said base and terminating in two ends, comprising:
at least one abutment, said abutment having a substantially spherical head, a neck connected to said head and a base connected to said neck, said neck having a diameter smaller than said head, said abutment having an abutment aperture extending inwardly from said base, said abutment aperture having internal threads,
an implant for each said abutment, said implant having a first end, a spaced second end, and external threads extending from said second end towards said first end for threading said implant into alveolar bone, said implant having an externally threaded abutment connecting member that projects from said first end, said abutment connecting member being sized and shaped to thread into said abutment aperture, to releasably, threadedly connect said first end of said implant to said base of said abutment,
an engaging cap for each said abutment rigidly mounted in said denture, said engaging cap having an end portion with a first face and a spaced second face opposite said first face, and an enclosing fence that projects transversely from said second face to define a cavity with an open end opposite said end portion, said cavity being sized to receive said head, said engaging cap including means, connected to said fence at said open end, for releasably retaining said head in said cavity, said cavity being sized longitudinally to define a space between said head and said end portion when said means for releasably retaining said head contacts said head, and
a resilient liner in said inner channel, said liner extending into said inner channel along said sides from said two ends to contact said engaging cap, said liner surrounding said engaging cap across said base of said inner channel, said liner supporting said denture on said gingival tissue, said liner compensating for the sponginess and surface irregularities in the gingival tissue so that the chewing forces are more uniformly distributed over the whole surface area of gingival tissue and said space is maintained during chewing, wherein said abutment has a height that is selected such that said liner supports said denture on said gingival tissue so that chewing forces on said denture are transmitted from said denture to said gingival tissue so that said space remains during chewing so that no chewing forces are transmitted from said denture to said abutment while said abutment restricts movement of said denture away from said gingival tissue.

\* \* \* \* \*